United States Patent [19]

Sih

[11] 4,251,464
[45] Feb. 17, 1981

[54] 2-DECARBOXY-2-AMINOMETHYL-19-HYDROXY-6-OXO-PGE$_1$ COMPOUNDS

[75] Inventor: John C. Sih, Kalamazoo, Mich.

[73] Assignee: The Upjohn Company, Kalamazoo, Mich.

[21] Appl. No.: 126,488

[22] Filed: Mar. 3, 1980

Related U.S. Application Data

[62] Division of Ser. No. 54,811, Jul. 5, 1979, Pat. No. 4,225,508.

[51] Int. Cl.$^3$ .................... C07C 91/14; C07C 91/40
[52] U.S. Cl. .................................. 564/453; 564/454
[58] Field of Search ............ 260/571, 573, 574, 570.9, 260/563 R

[56] References Cited

U.S. PATENT DOCUMENTS

| | | | |
|---|---|---|---|
| 3,849,474 | 11/1974 | Abraham et al. | 260/584 A X |
| 3,919,285 | 11/1975 | Axen | 560/121 |
| 3,935,240 | 1/1976 | Mallion | 260/571 X |
| 3,954,741 | 5/1976 | Schaaf et al. | 260/561 R X |
| 4,064,351 | 12/1977 | Sukai et al. | 260/574 X |

FOREIGN PATENT DOCUMENTS

2635985 2/1978 Fed. Rep. of Germany ........... 560/121

OTHER PUBLICATIONS

Johnson, "JACS", 100, pp. 7690–7704, (1978).

*Primary Examiner*—John Doll
*Attorney, Agent, or Firm*—Robert A. Armitage

[57] ABSTRACT

The present invention provides novel 2-decarboxy-2-aminomethyl-19-hydroxy-6-oxo-PGF$_1$ compounds which are useful for pharmacological purposes, e.g., anti-asthmatic indications.

1 Claim, No Drawings

2-DECARBOXY-2-AMINOMETHYL-19-HYDROXY-6-OXO-PGE₁ COMPOUNDS

DESCRIPTION

CROSS REFERENCE TO RELATED APPLICATION

The present invention is a divisional application of U.S. Ser. No. 054,811, filed July 5, 1979, now U.S. Pat. No. 4,225,508.

BACKGROUND OF THE INVENTION

The present invention provides novel prostacyclin analogs. Particularly, the present invention relates to prostacyclin analogs substituted at the C-19 position by hydroxy.

Particularly, the present invention relates to 2-decarboxy-2-aminomethyl-19-hydroxy-6-oxo-PGF$_1$ compounds. The novel prostacyclin analogs are useful for pharmacological purposes, e.g., as anti-asthmatic agents. The preparation and use of these compounds is incorporated here by reference from U.S. Pat. No. 4,225,508 filed July 5, 1979.

PRIOR ART

For background on prostacyclin, see for example R. A. Johnson, et al., Prostaglandins 12, 915-928 (1976) and R. A. Johnson, et al., J. Am. Chem. Soc. 100, 7690-7704 (1978), and, as to pharmacological activity, the references cited therein. For analogs of prostacyclin, see, for example, J. Fried, et al., Proc. Natl. Acad. Sci. U.S.A. 74, 2199-2203, K. C. Nicolaou, et al., J.C.S. Chem. Comm. 1977, 331-332, N. A. Nelson, J. Am. Chem. Soc. 99, 7362-7363 (1977), and K. Kojima, et al., Tetra. Letters, 1978, (1977), and K. Kojima, et al., Tetra. Letters, 1978, 3743-3746. Regarding the nomenclature for analogs of PGI$_2$, see R. A. Johnson, et al., Prostaglandins 15, 737-740 (1978).

SUMMARY OF THE INVENTION

The present invention particularly provides a prostacyclin-type compound of the formula

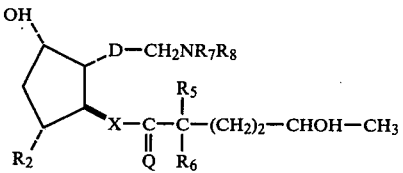

wherein D is —(CH$_1$)$_2$—CO-CH$_2$—L$_2$— or —CH$_2$—CO—CH$_2$-L$_3$— wherein L$_2$ is (1) —(CH$_2$)$_j$—, wherein j is one to 4, inclusive,
(2) —(CH$_2$)$_q$-CF$_2$—, wherein q is one, 2, or 3, or
(3) —CH=CH—, wherein L$_3$ is (1) -(CH$_2$)$_n$—, wherein n is one to 5, inclusive,
(2) —(CH$_2$)$_p$-CF$_2$—, wherein p is 2, 3, or 4, or
(3) —CH$_2$-CH=CH—;

wherein Q is oxo, α-H:β-H, α-OH:βR$_4$, or α-R$_4$:β-OH,
wherein R$_4$ is hydrogen or alkyl of one to 4 carbon atoms, inclusive,
wherein R$_2$ is hydrogen, hydroxyl, or hydroxymethyl,
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydroge or fluoro;
wherein R$_7$ and R$_8$ are hydrogen, alkyl of one to 12 carbon atoms, inclusive, benzyl, or phenyl, being the same or different; wherein X is (1) trans—CH=CH—,
(2) cis—CH=CH—,
(3) -CH=C—, or
(4) —CH$_2$CH$_2$—,

I claim:
1. A prostacyclin-type compound of the formula

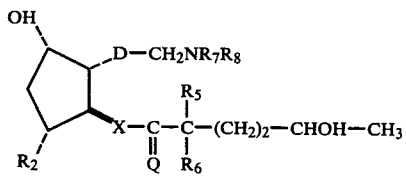

wherein D is —(CH$_2$)$_2$—CO-CH$_2$—L$_2$— or —CH$_2$—CO-CH$_2$—L$_3$— wherein L$_2$ is (1) —(CH$_2$)$_j$, wherein j is one to 4, inclusive,
(2) —(CH$_2$)$_q$—CF$_2$—, wherein q is one, 2, or 3, or
(3) —CH=CH—, wherein L$_3$ is (1) —(CH$_2$)$_n$—, wherein n is one to 5, inclusive,
(2) —(CH$_2$)$_p$-CF$_2$—, wherein p is 2, 3, or 4, or
(3) -CH$_2$-CH=CH—;

wherein Q is oxo, α-H:β-H, α-OH:β-R$_4$, or αR$_4$:β-OH,
wherein R$_4$ is hydrogen or alkyl of one to 4 carbon atoms, inclusive,
wherein R$_2$ is hydrogen, hydroxyl, or hydroxymethyl;
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro;
wherein R$_7$ and R$_8$ are hydrogen, alkyl of one to 12 carbon atoms, inclusive, benzyl, or phenyl, being the same or different; wherein X is (1) trans—CH=CH—,
(2) cis—CH=CH—,
(3) —C≡C—, or
(4) —CH$_2$CHP$_2$—.

* * * * *

UNITED STATES PATENT OFFICE
CERTIFICATE OF CORRECTION

Patent No. 4,251,464             Dated   17 February 1981

Inventor(s)  John C. Sih

It is certified that error appears in the above-identified patent and that said Letters Patent are hereby corrected as shown below:

In the title, "-PGE$_1$ COMPOUNDS" should read -- -PGF$_1$ COMPOUNDS --.

Column 1, line 54, "-(CH$_1$)$_2$-CO-CH$_2$-L$_2$-" should read
-- -(CH$_2$)$_2$-CO-CH$_2$-L$_2$- --;

Column 2, line 6, "α-OH:βR$_4$," should read -- α-OH:β-R$_4$, --; line 14, "hydroge or fluoro" should read -- hydrogen or fluoro --; line 20, "-CH=C-, or" should read -- -C≡C-, or --; line 42, "αR$_4$:β-OH," should read -- α-R$_4$:β-OH, --; line 56, "-CH$_2$CHP$_2$-." should read -- -CH$_2$CH$_2$-. --.

Signed and Sealed this

Eighteenth Day of August 1981

[SEAL]

Attest:

Attesting Officer

GERALD J. MOSSINGHOFF

Commissioner of Patents and Trademarks